United States Patent
Acemoglu et al.

(10) Patent No.: US 8,138,344 B2
(45) Date of Patent: Mar. 20, 2012

(54) PROCESS FOR THE PREPARATION OF RAPAMYCIN DERIVATIVES

(75) Inventors: Murat Acemoglu, Basel (CH); Sabine Pfeffer, Weil am Rhein (DE)

(73) Assignee: Novartis AG, Basel (CH)

( * ) Notice: Subject to any disclaimer, the term of this patent is extended or adjusted under 35 U.S.C. 154(b) by 835 days.

(21) Appl. No.: 12/160,110

(22) PCT Filed: Jan. 22, 2007

(86) PCT No.: PCT/EP2007/000514
§ 371 (c)(1),
(2), (4) Date: Jul. 7, 2008

(87) PCT Pub. No.: WO2007/085400
PCT Pub. Date: Aug. 2, 2007

(65) Prior Publication Data
US 2009/0012298 A1   Jan. 8, 2009

(30) Foreign Application Priority Data

Jan. 24, 2006  (GB) .................................. 0601406.2

(51) Int. Cl.
*C07D 491/16*  (2006.01)
*C07D 498/16*  (2006.01)
*A61K 31/436*  (2006.01)

(52) U.S. Cl. .......................... 546/90; 540/456; 514/291

(58) Field of Classification Search .................... 546/90, 546/207; 514/291; 540/456
See application file for complete search history.

(56) References Cited

U.S. PATENT DOCUMENTS
5,256,790 A   10/1993   Nelson

FOREIGN PATENT DOCUMENTS
WO     96/41807   12/1996

*Primary Examiner* — Jason M Nolan
(74) *Attorney, Agent, or Firm* — Carmella A. O'Gorman

(57) ABSTRACT

Processes for the production of a 32-deoxorapamycin from a 32-iodo- or 32-hydroxyrapamycin, wherein the hydroxy group is substituted by the residue of an arylthionocarbonate or an arylthiocarbamate, in the presence of tris(trimethylsilyl)-silan and α,α'-azo-isobutyronitril in organic solvent; and 32-deoxorapamycin in the form of a crystalline solvate.

6 Claims, 4 Drawing Sheets

PROCESS FOR THE PREPARATION OF RAPAMYCIN DERIVATIVES

Figure 1:
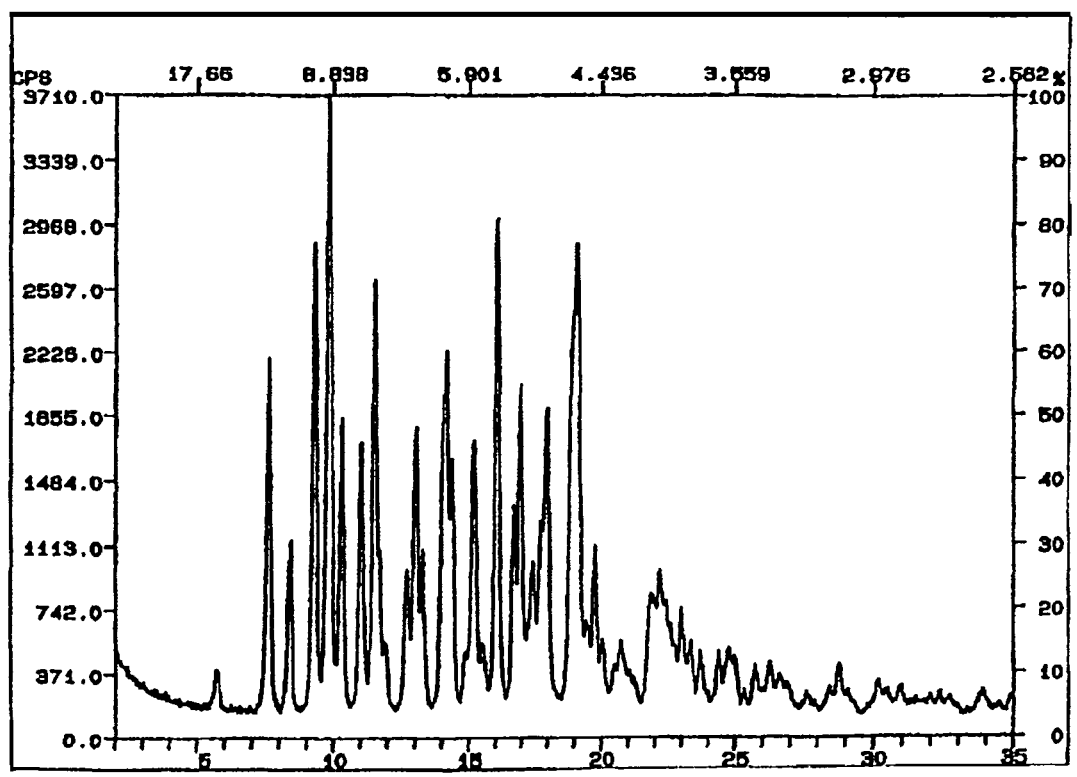

This is a National Stage of International Application No. PCT/EP2007/000514 filed Jan. 22, 2007, the entire disclosure of which is hereby incorporated by reference.

The present invention relates to a production process for organic compounds, e.g. including salts of organic compounds and processes for their production.

In WO9641807 there are described inter alia compounds of formula

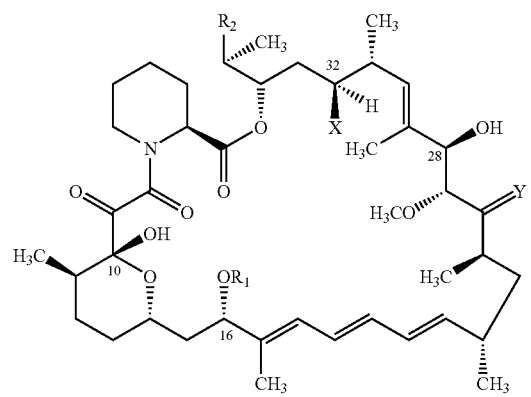

wherein
$R_1$ is alkyl, alkenyl, alkynyl, hydroxyalkyl, hydroxyalkenyl, hydroxyalkynyl, benzyl, alkoxybenzyl or chlorobenzyl,
$R_2$ is selected from a group of formula

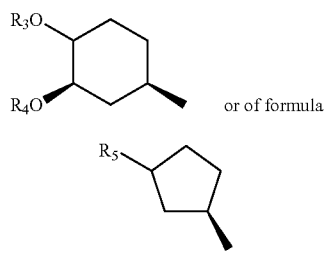

wherein
$R_3$ is selected from H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl and alkylsilyl;
$R_4$ is H, methyl or together with $R_3$ forms $C_{2-6}$ alkylene;
$R_5$ is $R_6O$—$CH_2$—, wherein
$R_6$ is selected from H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl and carbalkoxyalkyl;
$R_7CO$—, wherein
$R_7$ is selected from H, alkyl, hydroxy, alkoxy, aryloxy, amino, alkylamino, or N,N-disubstituted-amino wherein the substituents are selected from alkyl, aryl or arylalkyl;
$R_8NCH$—, wherein $R_8$ is alkyl, aryl, amino, alkylamino, arylamino, hydroxy, alkoxy or arylsulfonylamino; —O—CH—O— or substituted dioxymethylyne;
Y is selected from O, (H,OH), and (H,$OR_9$), wherein
$R_9$ is selected from $C_{1-4}$alkyl, alkylcarbonyl, arylcarbonyl, heteroarylcarbonyl, hydroxyalkylcarbonyl, aminoalkylcarbonyl, formyl or aryl; and
X is H or OH.

In WO9641807 there are furthermore described processes to obtain compounds of formula I wherein the residues are as defined above. A key step in the production for compounds of formula I wherein X is H, is the reduction of a carbonyl group in position 32 in a compound of formula I wherein a carbonyl group is attached to the C-atom in position 32 instead of X and H.

According to WO9641807 such process may be carried out according to several different methods, e.g. to produce a compound of formula I wherein X is H, by reduction of the carbonyl function in position 32 of a compound of formula

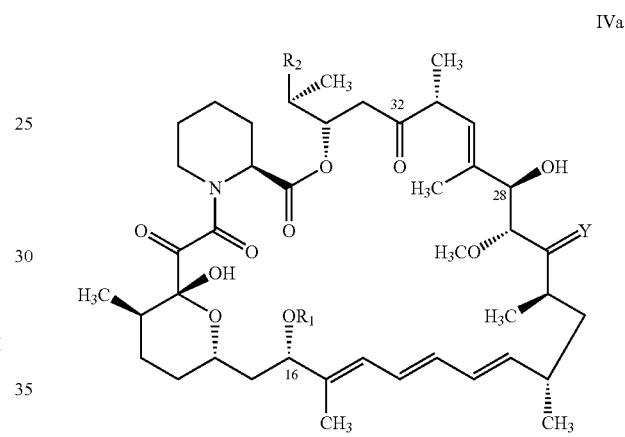

wherein $R_1$, $R_2$ and Y are as defined above, in protected or unprotected form, and, where required, removing the protecting groups present, e.g. and optionally converting a compound of formula I obtained, wherein $R_1$ is alkyl to provide a compound of formula I wherein $R_1$ is other than alkyl, e.g. by
(a) the reduction to the 32-deoxo compound of formula I may conveniently be performed by the following reaction sequence, namely
  i) by reacting a compound of formula IVa preferably in protected form with a hydride, e.g. diisobutyl aluminium hydride or preferably lithium tri-tert-butoxyaluminium hydride, to produce a corresponding 32-hydroxy compound (OH group in position 32 of the ring structure),
  followed by ii), namely by converting the 32-hydroxy compound into the corresponding 32-halo-derivative, e.g. 32-bromo- or (preferably) 32-iodo-derivative, which is then reduced e.g. by a hydride into the desired 32-deoxo derivative and, where required, deprotecting the resulting compound. Further reagents such as used for reducing halides may be used and include e.g. low valent metals (i.e. lithium, sodium, magnesium and zinc) and metal hydrides (aluminium hydrides, borohydrides, silanes, copper hydrides) (see Comprehensive Organic Transformations, R. C. Larock, VCH Publishers Inc., New York, 1989, pp. 18-20, sections 1.5.1. and 1.5.2.) (alternatively, halide reduction can be achieved by use of hydrogen or a hydrogen source (i.e. formic acid or a salt thereof) in the presence of a suitable metal catalyst (i.e. Raney-nickel, palladium metal or palladium complexes, complexes of rhodium or ruthenium) (see Comprehensive Organic Transformations, R. C. Larock, VCH Publishers Inc., New York, 1989, pp. 20-24, section 1.5.3.)).
(b) known methods as used for transforming an alcohol into the corresponding deoxy compound, may also be employed. These methods include e.g. direct reduction or reduction of an intermediate phosphorous compound, sulfonate, thiocarbonate, thiocarbamate or xanthate and are described e.g. in Comprehensive Organic Transformations, R. C. Larock, VCH Publishers Inc., New York, 1989, pp. 27-31, sections 1.9.1.-1.9.4); or
(c) the formation of a tosylhydrazone followed by treatment with a borane, e.g. catecholborane, or through the formation of a dithiane followed by suitable reduction, e.g. with Raney Nickel or a hydride, e.g. tributyltin hydride. Other known methods for transforming a ketone into the corresponding alcane may be used; such methods include e.g. direct reduction (see Comprehensive Organic Transformations, R. C. Larock, VCH Publishers Inc., New York, 1989, pp. 35-37, section 1.12.I) or reduction via hydrazones (Comprehensive Organic Transformations, R. C. Larock, VCH Publishers Inc., New York, 1989, pp. 37-38, section 1.12.2) and via sulfur and selenium derivatives (Comprehensive Organic Transformations, R. C. Larock, VCH Publishers Inc., New York, 1989, pp. 34-35, sections 1.10. and 1.1 L).

An exemplified process in WO9641807 to obtain 32-deoxorapamycin is the production of a compound of 32-hydroxy rapamycin-derivative in protected form, converting the hydroxy group in position 32 into a mesylate group, converting said mesylate group into an iodine group, treating the protected compound of formula I obtained wherein X is iodine with tributyl tin hydride and subsequent treating with a solution of triethylborane in hexane, purifying the protected 32-deoxo-compound obtained by column chromatography to obtain the protected 32-deoxo-compound in solid form and treating the protected 32-deoxo-compound obtained with sulfuric acid in methanol and subsequently with $NaHCO_3$ to obtain the unprotected 32-deoxo-compound, which unprotected 32-deoxo-compound may be obtained in crystalline form.

According to the present invention surprisingly it was found an improved process for the production of a compound of formula I, wherein X is H and $R_1$, $R_2$ and Y are as defined above, e.g. a process which is useful on technical scale.

In one aspect the present invention provides a process for the production of a compound of formula I wherein X is H and $R_1$, $R_2$ and Y are as defined above, comprising
A) either treating
a) a compound of formula V

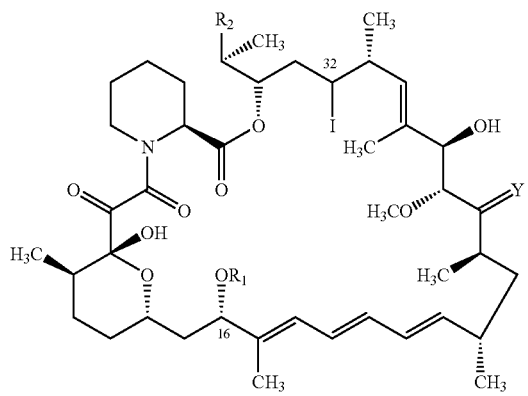

wherein $R_1$, $R_2$ and Y are as defined in a compound of formula I, and wherein reactive groups present are in unprotected, or in a protected form, preferably in a protected form, with tris(trimethylsilyl)-silan, a ($C_{6-18}$) alkylmercaptan, e.g. t-dodecylmercaptan and α,α'-azo-isobutyronitril in organic solvent, or
b) a compound of formula VI

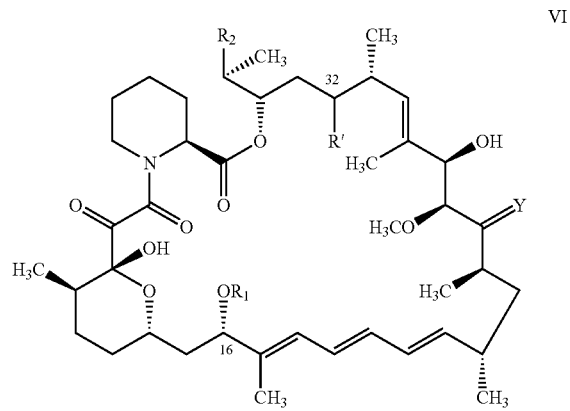

wherein $R_1$, $R_2$ and Y are as defined in a compound of formula I and wherein R' is a the residue of an arylthionocarbonate or arylthionocarbamate which arylthionocarbonate or arylthionocarbamate is bound to the C-atom in position 32 of the ring structure via the —O— atom, and wherein reactive groups present are unprotected, or in a protected form, preferably in a protected form, with tris(trimethylsilyl)-silan and α,α'-azo-isobutyronitril in organic solvent,
B) splitting off protective groups, if present,
C) isolating a compound of formula I wherein $R_1$, $R_2$ and Y are as defined above, and
D) optionally converting a compound of formula I obtained into another compound of formula I, e.g. converting a compound of formula I, wherein $R_1$ is alkyl, into another compound of formula I wherein $R_1$ is as defined above, but other than alkyl.

In a compound of formula VI an arylthionocarbonate or an arylthionocarbamate which is bound to the C-atom in position 32 to the ring structure via the —O— atom includes a group of formula VII

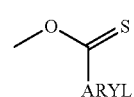

wherein ARYL is $C_{6-18}$aryloxy (residue of an arylthionocarbonate, or ARYL is arylic 5 or 6 membered heterocyclyl comprising 1 to 4 heteroatoms selected from N, O, S with the proviso that heterocyclyl comprises at least one N, which heterocyclyl is bound to the C=S group in a group of formula VII via a heterocyclic nitrogen atom (residue of an arylthionocarbamate).

$C_{6-18}$aryl includes phenyl, e.g. unsubstituted phenyl or substituted phenyl, preferably unsubstituted phenyl or phenyl substituted by groups which are inert under reaction conditions, e.g. phenyl substituted by halogen, e.g. fluoro.

Arylic 5 or 6 membered heterocyclyl comprising 1 to 4 heteroatoms selected from N, O, S with the proviso that it comprises at least one N, may be optionally annellated with another ring (system). Arylic heterocyclyl has preferably 5 ring members and is preferably imidazolyl.

In a compound of formula I a substituent comprising "alk" or "alkyl" refers to a $C_{1-10}$ aliphatic substituent optionally interrupted by an oxy linkage; and "ar" or "aryl" refers to a monocyclic, optionally heterocyclic, optionally substituted, $C_{4-14}$ aromatic substituent.

Examples of "ar" moiety or "aryl" mentioned above and optionally substituted may include e.g. phenyl, benzyl, tolyl, pyridyl and the like.

When $R_1$ is chlorobenzyl or alkoxybenzyl, the substituent is preferably in ortho.

When $R_7CO$— is N,N-disubstituted-carbamoyl, it may be e.g. N-methyl-N-(2-pyridin-2-y-ethyl)-carbamoyl, (4-methyl-piperazin-1-yl)-carbonyl or (morpholin-4-yl)-carbonyl.

When R, is substituted dioxymethylyne, it may be e.g. O,O-(alkylene)-dioxy-methylyne, i.e. wherein the 2 oxygens are linked by an alkylene group.

In a compound of formula I, the following significances are preferred either individually or in any combination or subcombination:

1. $R_1$ is $C_{1-10}$alkyl, $C_{3-10}$alk-2-enyl, $C_{3-10}$hydroxyalk-2-enyl, $C_{3-10}$alk-2-ynyl, $C_{3-10}$hydroxyalk-2-ynyl or $C_{1-10}$alkoxy$C_{1-10}$alkyl, preferably $C_{1-6}$alkyl or $C_{3-6}$alk-2-ynyl, more preferably $C_{1-4}$alkyl, most preferably methyl;

2. $R_1$ is $C_{3-6}$alk-2-ynyl as $R_1$ is 2-propynyl or pent-2-ynyl, preferably pent-2-ynyl;

3. Y is O, (H, OH) or (H, $C_{1-4}$alkoxy), preferably O;

4. $R_2$ is a group of formula II;

5. In the group of formula II, $R_3$ is H, $C_{1-6}$hydroxyalkyl, hydroxy-$C_{1-6}$alkoxy-$C_{1-6}$alkyl, ($C_{1-6}$alkyl)-carbonyl-amino-$C_{1-6}$alkyl, $C_{1-6}$alkoxy-$C_{1-6}$alkoxy or amino-$C_{1-6}$alkyl, preferably H, hydroxyethyl, hydroxypropyl, hydroxyethoxyethyl, methoxyethyl or acetylaminoethyl; especially H when $R_1$ is alkynyl;

6. In the group of formula II, $R_4$ is methyl.

7. $R_2$ is a residue of formula III wherein $R_5$ is $R_6OCH_2$— wherein $R_6$ is selected from H, $C_{1-6}$alkyl, $C_{3-6}$alk-2-enyl, $C_{3-6}$alk-2-ynyl, aryl, $C_{1-6}$alkylcarbonyl, arylcarbonyl, hydroxy$C_{1-6}$alkyl, $C_{1-6}$alkoxy-$C_{1-6}$alkyl, or amino$C_{1-6}$alkyl, $R_7CO$— wherein $R_7$ is selected from H, hydroxy, $C_{1-6}$alkoxy, amino, $C_{1-6}$alkylamino, a residue of an amino acid or N,N-disubstituted amino wherein the substituents are selected (a) from $C_{1-6}$alkyl or aryl or (b) from a heterocyclic structure;

$R_8NCH$— wherein $R_8$ is alkyl, aryl, amino, alkylamino, arylamino, hydroxy, alkoxy or arylsulfonylamino; —O—CH—O—; or substituted dioxymethylyne.

Especially preferred compounds of formula I include e.g. 16-O-pent-2-ynyl-32-deoxo-rapamycin; 16-O-pent-2-ynyl-32-deoxo-40-O-(2-hydroxy-ethyl)-rapamycin, and 32-deoxo-rapamycin; such as 32-deoxo-rapamycin of formula

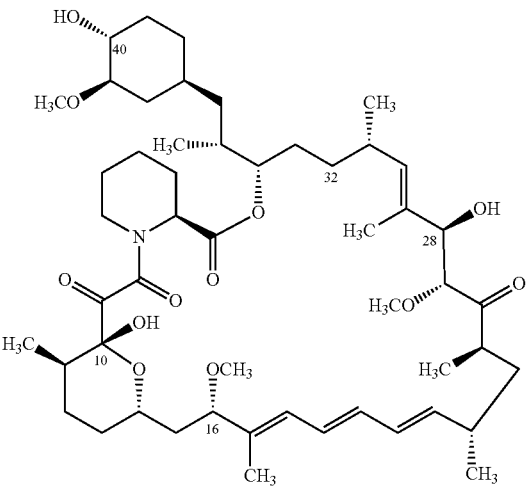

Compounds of formula I may exhibit isomerism and accordingly further isomeric forms will exist. It will be understood that the present invention embraces a compound of formula I in any individual isomeric form and any isomeric mixture, e.g. a compound of formula I in the form of the individual isomers and the individual isomers of formula

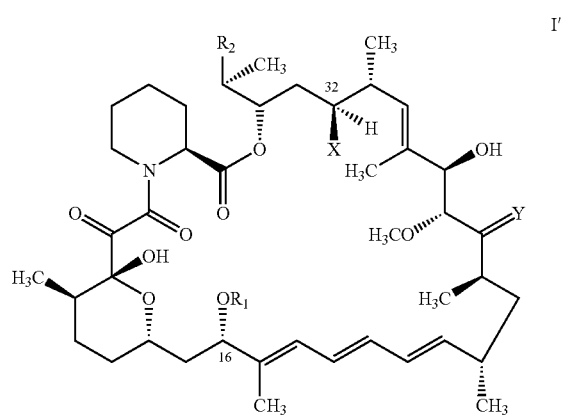

wherein $R_1$, $R_2$, Y and X are as defined above, as well as isomeric mixtures thereof. Individual isomers may be separated as appropriate, e.g. by a method as conventional.

A compound in protected from, as used herein, refers to a compound of a specified formula described herein, such as a compound of formula I, I', $I_p$, IVa, V and VI, wherein reactive groups are protected. Suitable protecting groups include appropriate protecting groups, e.g. such as conventional. Reactive groups e.g. include hydroxy groups, such as the hydroxy group in position 28, and, in case that $R_2$ is a compound of formula II, and $R_3$ is H, the hydroxy group attached to the ring system in position 40. It has been found, that the hydroxy group in position 10 of the ring structure in a compound of formula V is unreactive under the reaction conditions and does not need protection.

Hydroxy protecting groups and methods for protection and protecting group removal are e.g. disclosed in Protective Groups in Organic Synthesis, second ed., T. W. Greene and P. G. M. Wuts, John Wiley & Sons, New York, 1991, Chapter 2 and references therein. Preferred OH protecting groups are e.g. triorganosilyl groups such as tri($C_{1-6}$)alkylsilyl (e.g. trimethylsilyl, triethylsilyl), triiso-propylsilyl, isopropyldimethylsilyl, t-butyldimethylsilyl, triarylsilyl (e.g. triphenylsilyl) or triaralkylsilyl (e.g. tribenzylsilyl). Deprotection may be carried out under mildly acidic conditions.

Preferably the hydroxy groups in position 28 and 40 of the ring structure in a compound of formula I, I', $I_p$, IVa, V and VI are protected by triorganosilyl groups, more preferably by triethylsilyl.

Compounds of formula V, e.g. in protected form, used as a starting material according to the present invention may be obtained as appropriate, e.g. according, e.g. analogously, to a method as conventional. Compounds of formula V, e.g. in protected form, and their production are known e.g. from WO9641807.

Compounds of formula VI, e.g. in protected form, used as a starting material according to the present invention may be obtained as appropriate, e.g. according, e.g. analogously, to a method as conventional, or as described herein.

In another aspect the present invention provides a process for the production of a compound of formula VI, wherein R', $R_1$, $R_2$ and Y are as defined above, e.g. a compound of formula VI in protected form, comprising treating a compound of formula I, wherein X is hydroxy, and $R_1$, $R_2$ and Y are as defined above, e.g. in protected form, with an ary-chlorothionoformate, or an arylthionocarbamate in a reactive form, e.g. an ary-chloro-thionoformate of formula

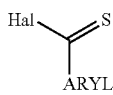

VIII wherein Hal is halogen, e.g. bromo, chloro, and ARYL is as defined above, or, in case of an arylthionocarbamate a compound of formula

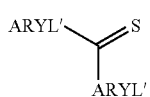

IX wherein both ARYL' independently of each other are arylic heterocyclyl as defined above under ARYL,
in organic solvent in the presence of a base and optionally in the presence of a condensation agent, such as an succinimide, e.g. N-hydroxysuccinimide, and
isolating a compound of formula VI obtained from the reaction mixture.

In a preferred embodiment the present invention provides a process according to the present invention according to step a) in steps A) to D) as described herein (herein also designated as A)a)-method). A compound of formula V is used as a starting material wherein reactive groups are preferably protected.

The A)a)-reaction according to the present invention may be carried out as follows:
The reaction is carried out in organic solvent. Appropriate organic solvent includes solvent which is inert under the reaction conditions, e.g. hydrocarbons, such as aliphatic, optionally halogenated hydrocarbons, aromatic or cycloaliphatic hydrocarbons; ethers, acetates, or individual mixtures of solvent cited. Preferably a solvent is chosen which, upon contact with water, may form a two phase system comprising an organic layer and an aqueous layer.

Preferred solvent include hydrocarbons, e.g. cyclic hydrocarbons, such as cyclohexane, and acetates, such as ethylacetate, propylacetate, isopropylacetate, e.g. isopropylacetate. Preferably a mixture of solvents is used, e.g. a mixture of hydrocarbons and acetates, such as a mixture of isopropylacetate and cyclohexane.

For carrying out the reaction a compound of formula V, preferably in protected form, is contacted with tris(trimethylsilyl)-silane, a ($C_{6-18}$)alkylmercaptan, e.g. t-dodecylmercaptan and α,α'-azo-isobutyronitril in organic solvent and reacted at appropriate temperature. Preferably tris(trimethylsilyl)-silan in organic solvent, e.g. a hydrocarbon, is treated with a compound of formula V in organic solvent, e.g. a hydrocarbon, an ($C_{6-18}$)alkylmercaptan is added and the mixture obtained is heated to appropriate temperature, e.g. a temperature range of (ca.) 50° C. to 80° C., more preferably to a temperature range of (ca.) 60° C. to 70° C. To the mixture obtained α,α'-azo-isobutyronitril in organic solvent, e.g. an acetate, is added, e.g. in portions and the mixture obtained is reacted until starting materials are under a pre-determined concentration range (HPLC control) (ca. 1 to 3 hours). An optionally protected compound of formula V, wherein X is H and $R_1$, $R_2$ and Y are as defined above, e.g. the hydroxy groups in position 28 and, if applicable, in position 40 of the ring system are protected by triorganosilyl, is obtained.

Removal of the protecting groups may be carried out as follows:
The mixture obtained is cooled to a temperature of −10° C. or below, e.g. a temperature range of (ca.) −30° C. to 0° C., such (ca.) −20° C. to −10° C., and a pre-cooled, polar, organic solvent is added. Polar organic solvent includes e.g. alcohols, such as methanol. The mixture obtained is stirred at a temperature of −10° C. to −20° C. until starting materials are under a pre-determined concentration range (e.g. (ca.) 0.25 to 2 hours). A compound of formula I, wherein $R_1$, $R_2$ and Y are as defined above, such as a compound of formula $I_p$, s obtained in unprotected form.

Work-up of the reaction mixture may be carried out as follows:
To the mixture obtained a base is added to obtain a pH of the mixture of ca. 7. A base includes inorganic bases, e.g. a salt of sodium or potassium, preferably sodium or potassium hydrogencarbonate. The base is added, preferably in solution, more preferably in aqueous solution, e.g. in such a way, that the temperature does not exceed a temperature range of −20° C. to −10° C. To the mixture obtained organic solvent which, upon contact with water, may form a two phase system comprising an organic layer and an aqueous layer, e.g. such as described above for the reaction to obtain a protected compound of formula I, and water is added. Such organic solvent is preferably an acetate. The mixture obtained is stirred and the phases obtained are separated. If desired, the aqueous phase is further extracted with organic solvent and the organic layers obtained are combined. From the organic layer solvent is evaporated under reduced pressure. A compound of formula I is obtained, wherein $R_1$, $R_2$ and Y are as defined above, e.g. a compound of formula $I_p$, e.g. in the form of an oil.

In another preferred embodiment the present invention provides a process according to the present invention according to step b) in steps A) to D) as described herein (herein also designated as A)b)-method). A compound of formula VI is used as a starting material wherein reactive groups are preferably protected.

The A)b)-method according to the present invention may be carried out as follows:

The reaction is carried out in organic solvent. Appropriate organic solvent includes solvent as described for the A)a) reaction above, such as aromatic hydrocarbons, e.g. toluene. For carrying out the reaction a compound of formula VI, preferably in protected form, is contacted with tris(trimethylsilyl)-silan, a ($C_{6-18}$)alkylmercaptan, e.g. t-dodecylmercaptan and α,α'-azo-isobutyronitril in organic solvent and reacted at appropriate temperature. Preferably a compound of formula VI in a mixture of organic solvent with a ($C_{6-18}$) alkylmercaptan, is heated, e.g. to a temperature range of (ca.) 80° C. to 110° C., such as (ca.) 95° C. to 105° C. and tris (trimethylsilyl)-silan and α,α'-azo-isobutyronitril in organic solvent are added and the mixture obtained is reacted until starting materials are under a pre-determined concentration range (HPLC control) (ca. up to 1 hour). An optionally protected compound of formula VI, wherein X is H and $R_1$, $R_2$ and Y are as defined above, e.g. the hydroxy groups in position 28 and, if applicable, in position 40 of the ring system, are protected by triorganosilyl, e.g. by triethylsilyl, is obtained.

Removal of the protecting groups may be carried out as described in WO9641807. A compound of formula I, wherein $R_1$, $R_2$ and Y are as defined above is obtained in unprotected form.

Work-up of the reaction mixture may be carried out as described in the A)a)-method above, but using as a preferred solvent a aromatic hydrocarbon, such as toluene.

A compound of formula I is obtained, wherein $R_1$, $R_2$ and Y are as defined above, e.g. in the form of an oil.

A compound of formula I obtained according to any of method A)a) or method A)b) may be further purified by a method as appropriate, e.g. by chromatography, such as column chromatography.

Chromatography may be carried out via column chromatography on silica gel 60, using an appropriate solvent mixture as a mobile phase, such as a mixture of an acetate and a hydrocarbon, e.g. a mixture of ethyl acetate and n-hexane, e.g. ethyl acetate:n-hexane 2:1. A compound of formula I may be obtained in solid form, e.g. by addition of an anti-solvent to fractions comprising a compound of formula I.

It was furthermore found that a compound of formula $I_p$ may also be obtained in crystalline form, e.g. by addition of n-heptane to fractions comprising a compound of formula $I_p$ obtained from chromatography.

According to the present invention surprisingly it was further found that a compound of formula $I_p$ may also be obtained in the form of a solvate with an organic solvent, such as an acetone solvate or a solvate with propylene glycol, or a solvate with water, e.g. a hydrate, such as a monohydrate, if acetone, propylene glycol, or water, respectively, is present in the solvent crystallization mixture.

The crystal form of a compound of formula $I_p$ obtained when acetone is present in the crystallization solvent mixture is designated herein as Form A (acetone solvate) and the crystal form of the hydrate of a compound of formula $I_p$ obtained when water is present in the crystallization solvent mixture as Form B. Furthermore it was found that another monohydrate form of a compound of formula $I_p$, designated as Form 2, may be obtained, if water and methanol is present in the crystallization solvent mixture. On heating Form 2 transforms reversibly into an anhydrous Form 2'.

It was found that Form B may be obtained if an alcohol, e.g. methanol or ethanol is present in the crystallization solvent mixture and water is used as an anti-solvent. It was found that Form A may be obtained if acetone in the crystallization solvent mixture and an organic anti-solvent, e.g. a hydrocarbon such as hexane, is present in the crystallization solvent mixture It was also found that from both modifications, Form A and Form B, an anhydrous Form 1A' can be obtained on heating.

In another aspect the present invention provides a compound of formula $I_p$ in crystalline form in the form of a solvate, e.g. in the form of a solvate with an organic solvent, such as an acetone solvate or a propylene glycol solvate, e.g. in the form of a solvate with water, such as a hydrate, e.g. a monohydrate.

The X ray powder diffraction patterns of crystalline compounds provided according to the present invention are set out on FIG. 1 (acetone solvate)

Figure 2:
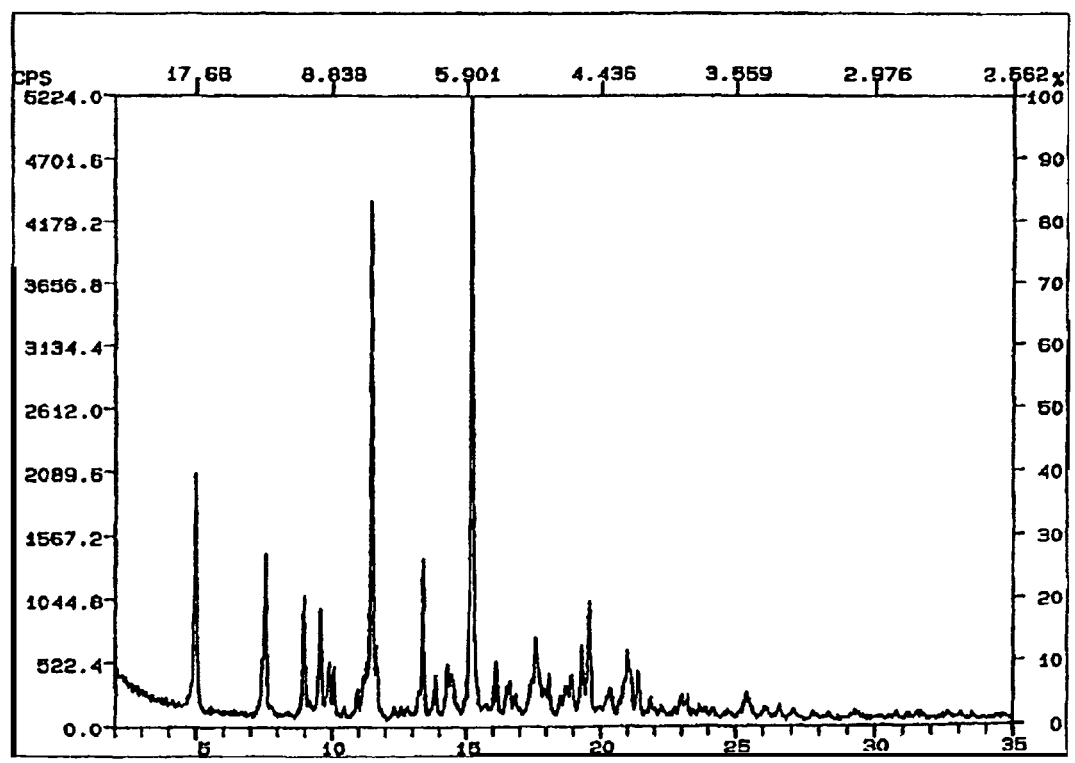

FIG. 2 (propylene glycol solvate)

Figure 3:
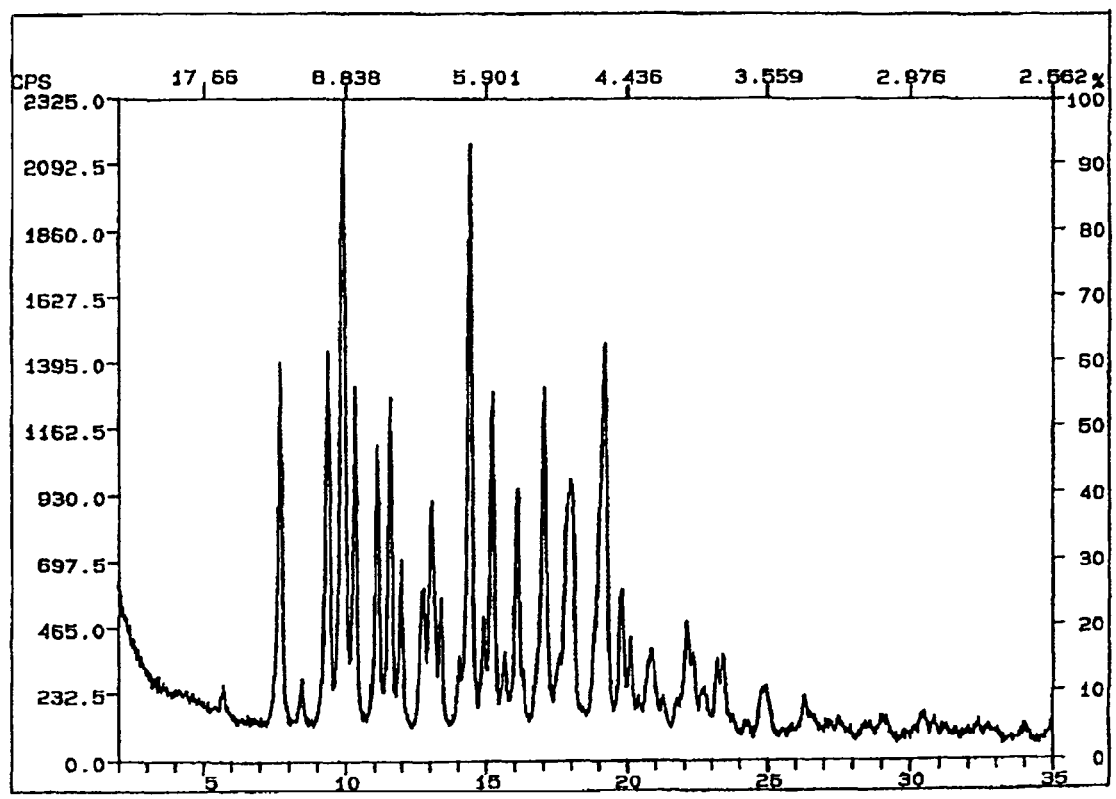

FIG. 3 (hydrate, Form 1)

Figure 4:
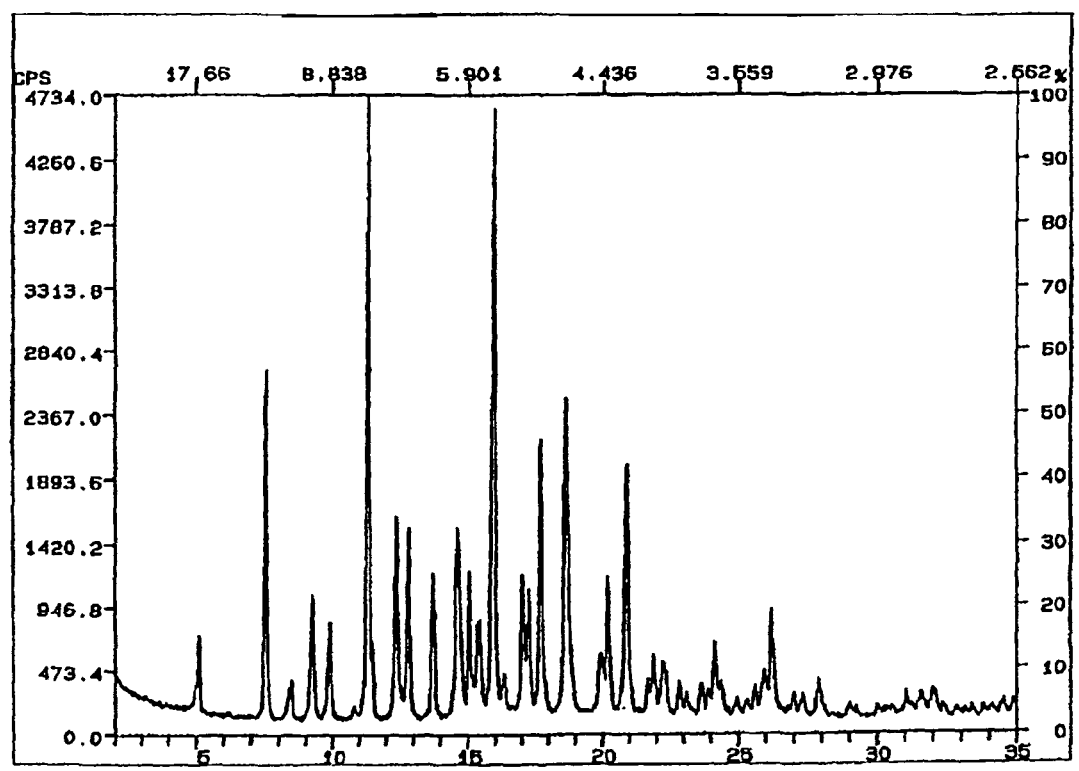

FIG. 4 (hydrate Form 2)

In FIGS. 1 to 4 the x-axis designates the diffraction angle, the y-axis designates the intensity measured. Wavelength: 1.54060.

In the following Examples all temperatures are in ° C.

32-Deoxorapamycin is a compound of formula $I_p$.

The compound 28,40-O-bis(triethylsilyl)-32-iodo-rapamycin is a compound of formula

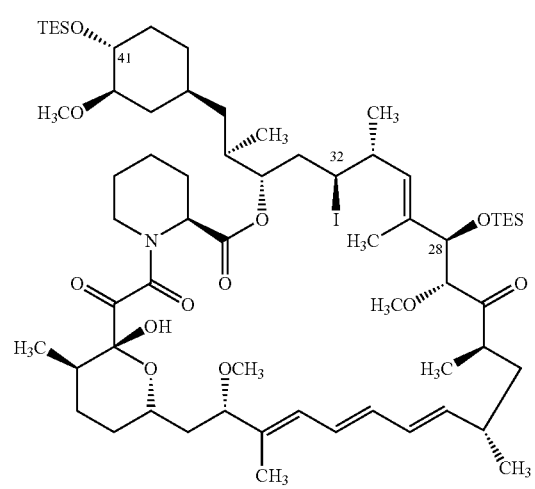

The compound 28,40-O-bis(triethylsilyl)-32-hydroxy-rapamycin is a compound of formula

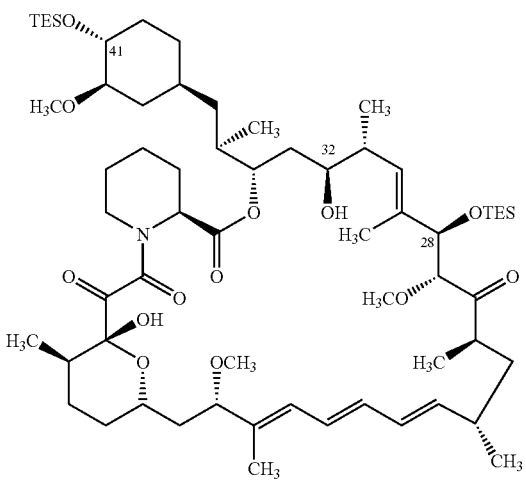

TES is the group triethylsilyl.

EXAMPLE 1

32-Deoxo-rapamycin in Crystalline Form

A) 28,40-O-Bis-(triethylsilyl)-32-deoxo-rapamycin

Under argon to a mixture of 1.74 g of tris(trimethylsilyl) silan in 5 g of cyclohexane a solution of 8.5 g of 28,40-bis-O-(triethylsilyl)-32-iodo-rapamycin in 70.6 g of cyclohexane and 14.44 g of t-dodecylmercaptane are added and the mixture obtained is heated to a temperature of around 65°. To the mixture obtained 0.1135 g of α,α'-azo-isobutyronitril (AIBN) in 7.4 g of isopropylacetate are added in portions, thereby keeping a temperature of around 65°. 28,40-O-bis (triethylsilyl)-32-deoxo-rapamycin is obtained.

B) 32-deoxo-rapamycin

The mixture obtained in step A is cooled to <–20° and poured onto 90 g of methanol, pre-cooled to –20°, thereby not exceeding a temperature of around –15°. The mixture obtained is stirred for ca. one hour and treated with 44.4 g of an aqueous, saturated $NaHCO_3$ solution°, thereby not exceeding a temperature of around –15°. The mixture obtained is stirred for ca. 15 minutes and treated with 68 g of isopropylacetate and 84.5 g of water. The mixture obtained is vigorously stirred and warmed up to room temperature. The phases are separated, the aqueous phase is extracted with isopropylacetate and the combined organic phases are washed with water. From the organic phase isopropyl acetate is distilled off under reduced pressure. An oil is obtained which is treated with 116 g of n-heptane. 32-Deoxorapamycin precipitates and is filtered off. 4.28 g of solid 32 deoxorapamycin in wet form and from the filtrate further 0.435 g of 32-deoxorapamycin in wet form are obtained. In total, 4.715 g of 32-deoxorapamycin in wet form comprising 3.080 g of 32-deoxorapamycin.

C) Purification of 32-deoxorapamycin

A column filled with 118 g of silica gel is treated with 3.98 g of 32-deoxorapamycin obtained according to a method as set out in step B), dissolved in a mixture of ethyl acetate: hexane=2:1. The fractions comprising 32-deoxorapamycin are collected and solvent is evaporated to a volume of ca. 10 ml.

D) Crystallization of 32-deoxorapamycin

To the evaporation residue obtained in step C) ca. 7 ml of ethyl acetate are added and to the mixture obtained ca. 20 ml of n-heptane are added dropwise. The mixture obtained is seeded with pre-prepared crystals of 32-deoxorapamycin and the mixture obtained is cooled to ca. 0° to 5° and stirred for ca. 1 hour. Crystallized 32-deoxorapamycin is isolated by filtration and dried. Yield: 1.69 g (ca, 74% of theory); purity more than 98%. M.p. in DSC: 127° C. (onset). XRD analysis of the crystals indicates that 32-deoxorapamycin obtained is in hydrate Form 1. From the filtrate obtained further crystallized 32-deoxorapamycin may be obtained.

According to the procedure described in steps A) to D) but using appropriate amount of starting materials, several kg's of crystalline 32-deoxorapamycin in hydrate Form 1 are obtained in a pilot plant.

E) Crystallization of 32-deoxorapamycin in the Form of an Acetone Solvate

Is obtained by cooling and precipitation from a diethyl ether and hexane fraction under addition of acetone, or by crystallization from acetone.

F) Crystallization of 32-deoxorapamycin in the Form of a Propylene Glycol Solvate Is obtained by cooling and precipitation from a diethyl ether and hexane fraction under addition of propylene glycol, or by crystallization from propylene glycol.

G) Crystallization of 32-deoxorapamycin in the Form of a Monohydrate

Is obtained from solvent, e.g methanol, comprising water (Form 2). Is also obtained after storage of an acetone solvate under high humidity conditions. Form 1 may be obtained from solvent, other than methanol, comprising water.

EXAMPLE 2

Production of 32-deoxorapamycin 1 g of a Compound of Formula $I_{EX}$

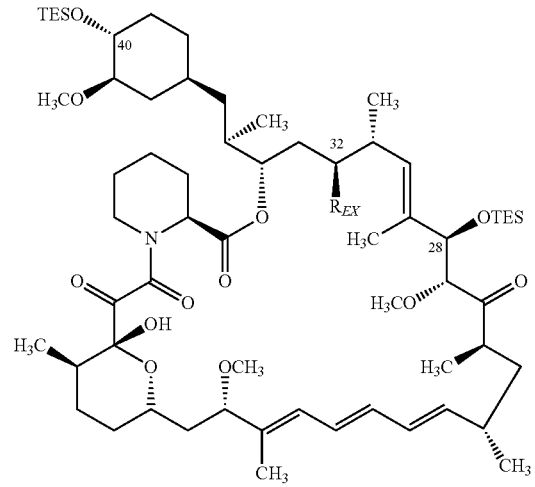

wherein $R_{EX}$ is a group of formula

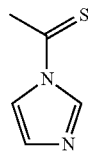

$IV_{EX}$ is dissolved in a mixture of 10 ml of dodecylmercaptane and 10 ml of toluene. The mixture obtained is heated to 100° and 0.407 g of tris(trimethylsilyl)silane are added at 100°, followed by the addition of a solution of 0.0262 g of AIBN in 1 ml of toluene at the same temperature. The mixture obtained is stirred for ca. 15 minutes at 100° and cooled to 5-10°. The mixture is slowly added to 20 ml of pre-cooled methanol, maintaining a temperature between −10 to −20° C. during addition. To the mixture obtained 25 ml of toluene is added and the mixture obtained is allowed to warm up to room temperature. The mixture obtained is extracted with aqueous, saturated $NaHCO_3$ solution and water. The aqueous layer obtained is extracted with toluene, the organic layers are combined, dried over sodium sulfate and solvent is evaporated. Crude 28,40-O-bis(triethylsilyl)-32-deoxorapamycin is obtained in the form of a yellowish solution. The solution obtained is subjected to flash chromatography on silica gel starting with hexane, followed by hexane:t-butyl-methyl ether=3:1. 0.573 g of 28,40-O-bis(triethylsilyl)-32-deoxorapamycin is obtained in the form of a white foam, in high purity (ca. 98%). 28,40-O-Bis(triethylsilyl)-32-deoxorapamycin thus obtained is treated with 2N aqueous sulfuric acid in methanol (according to the procedure as described in WO9641807). 32-Deoxorapamycin is obtained in high purity.

Production of Starting Materials

EXAMPLE A

Production of a Compound of Formula $I_{Ex}$, Wherein $R_{EX}$ is a Group of Formula

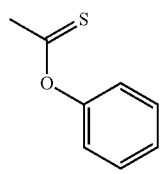

$II_{EX}$ 4.0 g of 28,40-O-bis(triethylsilyl)-32-hydroxy-rapamycin in 40 ml of $CH_2Cl_2$ are treated with 2.75 g of pyridine and 43 mg of 4-dimethylamino-pyridine at room temperature. To the mixture obtained 1.275 g of phenyl-chlorothionoformate is added and the mixture obtained is stirred for 7 hours at room temperature. The mixture obtained is subjected to chromatography on silica gel (eluted with methyl-t-butylether). A compound of formula $I_{EX}$, wherein $R_{EX}$ is a group of formula $II_{EX}$ is obtained in the form of a white foam. MS (Electrospray negative mode): 1324.8 $(M+HCOO)^-$, 1278.9 $(M-H)^-$. $^1H$-NMR confirms the proposed structure.

EXAMPLE B

Production of a Compound of Formula $I_{EX}$, Wherein $R_{EX}$ is a Group of Formula

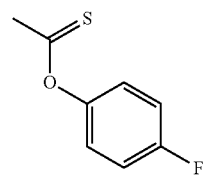

$III_{EX}$ 5.0 g of 28,40-O-bis(triethylsilyl)-32-hydroxy-rapamycin in 45 ml of $CH_2Cl_2$ are treated with 0.052 g of N-hydroxy-succinimide and 1.04 g of pyridine. To the mixture obtained 1.70 g of 4-fluorophenyl-chlorothionoformate are added dropwise such that the temperature does not exceed 30°. The mixture obtained is stirred for 3.5 hours at room temperature, poured onto 80 ml of dichloromethane and the mixture obtained is extracted with water. The organic layer obtained is washed with a saturated aqueous $NaHCO_3$-solution and $H_2O$, dried and solvent is evaporated to obtain a concentrated solution in $CH_2Cl_2$ (ca. 40 ml). To the solution obtained 60 ml of t-butyl-methyl ether is added and solvent is evaporated to a final volume of ca. 25 ml. Precipitation occurs. The suspension obtained is cooled to 0-5° for 45 minutes and the precipitate is removed by filtration. The filtrate obtained is concentrated by evaporation and the concentration residue is subjected to chromatography on silica gel. A compound of formula $I_{EX}$, wherein $R_{EX}$ is a group of formula $III_{EX}$ is obtained in the form of a foam. MS (FAB): 1304 $(M+Li)^+$. IR (KBr): 3420 broad, 2956, 2936, 2876, 1746, 1627, 1504, 1458, 1376, 1294, 1242, 1191, 1145, 1107, 1007, 988, 742 $cm^{-1}$. NMR spectra confirm the proposed structure.

EXAMPLE C

Production of a Compound of Formula $I_{EX}$, Wherein $R_{EX}$ is a Group of Formula $IV_{EX}$ 50 g of 28,40-O-bis(triethylsilyl)-32-hydroxy-rapamycin in 500 ml of toluene are treated with 11.7 g of 1,1-thiocarbonyl-diimidazole and 533.6 mg of 4-dimethylamino-pyridine, the solution obtained is warmed to 40° and stirred for 20 hours at this temperature. To the mixture obtained further 0.778 g of 1,1-thiocarbonyl-diimidazole are added and the mixture obtained is stirred for 2 hours at 40°. The mixture obtained is cooled to 0° and treated with an aqueous saturated solution of $NaHCO_3$. The layers obtained are separated and the organic layer is extracted with aqueous saturated $NaHCO_3$ solution and with $H_2O$. The organic layer obtained is subjected to chromatography on silica gel using first toluene and subsequently a 1:1 mixture of t-butyl-methyl ether/hexane as eluent. Solvent is evaporated and 46.1 g of a compound of formula $I_{EX}$, wherein $R_{EX}$ is a group of formula $IV_{EX}$ are obtained in the form a foam. MS (Electrospray positive mode): 1254.8 $(M+H)^+$, 1222.8 $(M-OCH_3)^+$. IR (KBr): 3428 broad, 3133, 2936, 2876, 2824, 1746, 1730, 1650, 1626, 1532, 1460, 1415, 1387, 1326, 1285, 1232, 1192, 1167, 1142, 1107, 1075, 1005, 988, 890, 867, 824, 742, 656, 642, 613 and 560 cm$^{-1}$. NMR spectra of the product confirm the proposed structure.

The invention claimed is:
1. A process for the production of a compound of formula I:

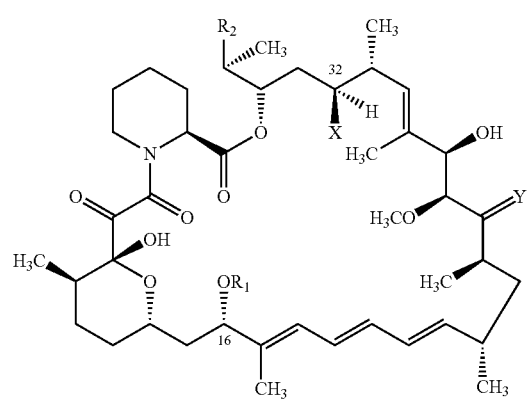

wherein
R$_1$ is alkyl, alkenyl, alkynyl, hydroxyalkyl, hydroxyalkenyl, hydroxyalkynyl, benzyl, alkoxybenzyl or chlorobenzyl,
R$_2$ is a compound of formula II or III:

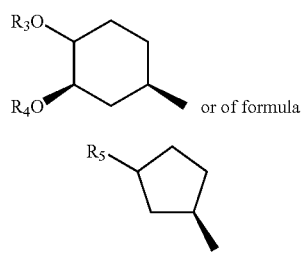

wherein
R$_3$ is selected from H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl and alkylsilyl;
R$_4$ is H, methyl or together with R$_3$ forms C$_{2-6}$ alkylene;
R$_5$ is R$_6$O—CH$_2$—, wherein
R$_6$ is selected from H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl and carbalkoxyalkyl;

Y is selected from O, (H, OH), and (H, OR$_9$), wherein
R$_9$ is selected from C$_{1-4}$alkyl, alkylcarbonyl, arylcarbonyl, heteroarylcarbonyl, hydroxyalkylcarbonyl, aminoalkylcarbonyl, formyl or aryl; and,
X is H,
the process comprising
A) treating a compound of formula IV:

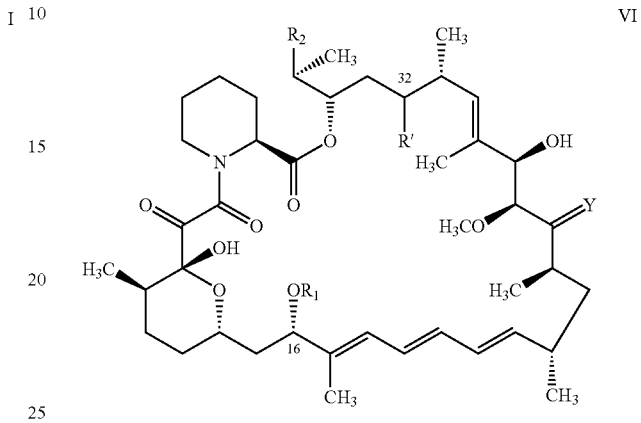

wherein R$_1$, R$_2$ and Y are as defined above and wherein R' is a the residue of an arylthionocarbonate or arylthionocarbamate which arylthionocarbonate or arylthionocarbamate is bound to the C-atom in position 32 of the ring structure via the —O— group, and wherein reactive groups are in unprotected or protected form, with tris(trimethylsilyl)-silan and α,α'-azo-isobutyronitril in organic solvent;
B) optionally splitting off protective groups, if present;
C) isolating a compound of formula I wherein R$_1$, R$_2$ and Y are as defined above; and
D) optionally converting a compound of formula I wherein R$_1$ is alkyl into a compound of formula I wherein R$_1$ is as defined above but not alkyl.
2. A process according to claim 1, wherein the compound of formula VI is in a protected form.
3. A process for the production of a compound of formula VI:

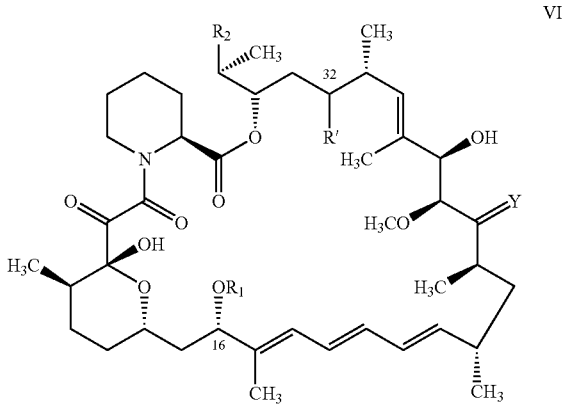

wherein
R$_1$ is alkyl, alkenyl, alkynyl, hydroxyalkyl, hydroxyalkenyl, hydroalkynyl, benzyl, alkoxybenzyl or chlorobenzyl, $R_2$ is selected from a compound of formula

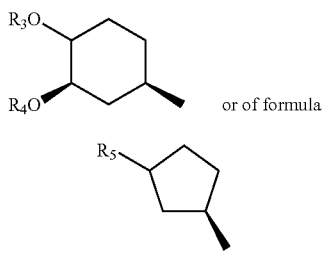

wherein:
$R_3$ is selected from H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl and alkylsilyl;
$R_4$ is H, methyl or together with $R_3$ forms $C_{2-6}$ alkylene;
$R_5$ is $R_6O-CH_2-$, wherein
$R_6$ is selected from H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl and carbalkoxyalkyl;
Y is selected from 0 (H, OH), and (H, $OR_9$), wherein $R_9$ is selected from $C_{1-4}$-alkyl, alkylcarbonyl, arylcarbonyl, heteroarylcarbonyl, hydroxyalkylcarbonyl, aminoalkylcarbonyl, formyl or aryl; and,
R' is a residue of an arylthionocarbonate or arylthionocarbamate, which arylthionocarbonate or arylthionocarbamate is bound to the C-atom in position 32 of the ring structure via the —O— atom, in protected form, comprising treating a compound of formula I,

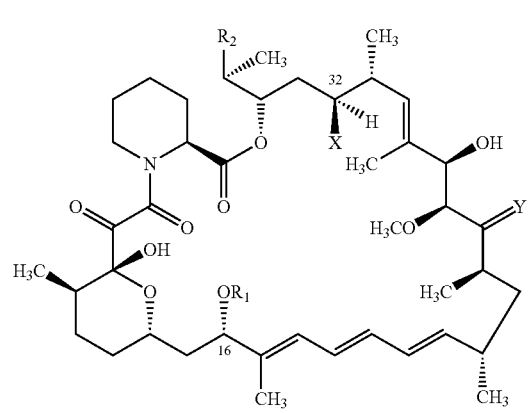

wherein X is hydroxy, and $R_1$, $R_2$ and Y are as defined above,
with an arylthionocarbonate where compound I is in a protected form; or, where the compound of formula I is in a reactive form:
an arylthionocarbamate:
an arylthionocarbamate of the formula VIII:

wherein Hal is halogen, and ARYL is $C_{6-18}$aryloxy or an arylic 5 or 6 membered heterocyclyl comprising 1 to 4 heteroatoms selected from N, O, S with the proviso that the heterocyclyl comprises at least one N, which heterocyclyl is bound to the C=S group in a the compound of formula VII:

via a heterocyclic nitrogen atom; or,
an arylthionocarbamate of formula IX:

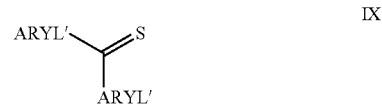

wherein each ARYL' is independently arylic heterocyclyl as defined above under ARYL;
in organic solvent in the presence of a base and optionally in the presence of a condensation agent, selected from the group consisting of succinimide, N-hydroxysuccinimide, and 4-dimethylaminopyridine; and
isolating compound of formula VI.

4. 32-Deoxorapamycin, in crystalline form in the form of an acetone solvate.

5. 32-Deoxorapamycin, in crystalline form in the form of a propylene glycol solvate.

6. 32-Deoxorapamycin in crystalline form in the form of a hydrate.

* * * * *